United States Patent [19]

Jakobsen et al.

[11] Patent Number: 5,145,870

[45] Date of Patent: * Sep. 8, 1992

[54] ARYLOXYPHENYLPROPYLAMINES THEIR PREPARATION AND USE

[75] Inventors: Palle Jakobsen; Jorgen Drejer, both of Vaerlose, Denmark

[73] Assignee: Novo Nordisk A/S, Bagsvaerd, Denmark

[*] Notice: The portion of the term of this patent subsequent to Oct. 9, 2007 has been disclaimed.

[21] Appl. No.: 529,004

[22] Filed: May 24, 1990

[30] Foreign Application Priority Data

May 26, 1989 [DK] Denmark .................. 2583/89

[51] Int. Cl.$^5$ .............. A61K 31/135; A61K 31/275; A61K 31/34
[52] U.S. Cl. ................................ 514/524; 514/469; 514/470; 514/652; 558/422; 564/352; 564/353
[58] Field of Search ............. 558/422; 564/352, 353; 514/524, 652, 469

[56] References Cited

U.S. PATENT DOCUMENTS

| | | | |
|---|---|---|---|
| 3,095,449 | 6/1963 | Wirth et al. | 564/353 |
| 4,194,009 | 3/1980 | Molloy et al. | 564/352 X |
| 4,296,126 | 10/1981 | Nedelec et al. | 564/347 X |
| 4,314,081 | 2/1982 | Molloy et al. | 564/347 |
| 4,327,214 | 4/1982 | Rentzea et al. | 564/352 X |
| 4,376,123 | 3/1983 | Hausberg et al. | 564/352 X |
| 4,956,388 | 9/1990 | Robertson et al. | 564/352 X |
| 4,962,122 | 10/1990 | Jakobsen et al. | 514/466 |
| 4,970,232 | 11/1990 | Jakobsen et al. | 514/466 |
| 5,019,592 | 5/1991 | Jakobsen et al. | 514/524 |

FOREIGN PATENT DOCUMENTS 0288188 10/1988 European Pat. Off. ............ 564/352

*Primary Examiner*—Joseph Paul Brust
*Attorney, Agent, or Firm*—Steve T. Zelson; Elias J. Lambiris

[57] ABSTRACT

Novel aryloxyphenylpropylamines having the formula

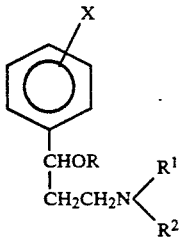

(I)

wherein

X is H, cyano, halogen, halogenoalkyl, $C_{1-6}$-alkoxy, $C_{1-6}$-alkyl, $C_{1-5}$-alkanoyl, $C_{3-5}$-alkylene, aryloxy or aralkoxy, and R is 3,4-methylenedioxy, aryl or heteroaryl which are optionally substituted with one or more cyano, halogeno, $C_{1-6}$-alkyl, $C_{1-6}$-alkoxy, $C_{1-6}$-alkenyl, trifluoromethyl, $C_{3-5}$-alkylene, aryloxy or aralkoxy; and $R^1$ and $R^2$ independently is $C_{1-10}$-alkyl, $C_{3-7}$-cycloalkyl, $C_{2-10}$-alkenyl, $C_{3-6}$-cycloalkyl-$C_{1-5}$-alkyl, optionally substituted with $C_{1-5}$-alkoxy or cyano;

$R^1$ and $R^2$ may together form a carbocyclic ring and a salt thereof with a pharmaceutically acceptable acid, provided however that $R^1$ is not $C_{3-7}$-cycloalkyl, $C_{1-10}$-alkyl, or alkenyl which may be straight, branched or cyclic, unsubstituted or substituted with $C_{1-4}$-alkoxy, aryloxy or cycloalkyl or cycloalkylalkyl, when X is H and $R^2$ is a methyl group.

The novel compounds are useful in the treatment of anoxia, migraine, ischemia, epilepsy, traumatic injury and neurodegenerative diseases.

5 Claims, No Drawings

ARYLOXYPHENYLPROPYLAMINES THEIR PREPARATION AND USE

The present invention relates to therapeutically active aryloxyphenylpropylamines, a method of preparing the same and to pharmaceutical compositions comprising the compounds. The novel compounds are useful in the treatment of anoxia, ischemia, migraine and epilepsy.

It is well known that accumulation of calcium in the brain cells (calcium overload) is seen after periods of uncontrolled hyperactivity in the brain, such as after convulsions, migraine, anoxia and ischemia. As the concentration of calcium in the cells is of vital importance for the regulation of cell function, an uncontrolled high concentration of the cell calcium will lead to, or indirectly cause the symptoms and possibly also the degenerative changes combined with the above diseases.

Therefore calcium overload blockers selective for brain cells will be useful in the treatment of anoxia, ischemia, migraine and epilepsy.

Well known calcium antagonists such as nifedipine, verapamil and diltiazem have activity against pheripheral calcium uptake, e.g. in blood vessels and the heart, however have shown only, very low activity against calcium overload in brain cells.

Accordingly it is an object of the invention to provide novel compounds having activity against calcium overload in brain cells.

The novel compounds of the invention are aryloxyphenylpropylamines having the general formula I

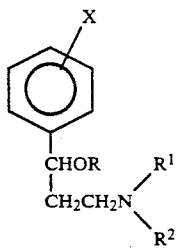

wherein

X is H, cyano, halogen, halogenoalkyl, $C_{1-6}$-alkoxy, $C_{1-6}$-alkyl, $C_{1-5}$-alkanoyl, $C_{3-5}$-alkylene, aryloxy or aralkoxy, and R is 3,4-methylenedioxy, aryl or heteroaryl which are optionally substituted with one or more cyano, halogeno, $C_{1-6}$-alkyl, $C_{1-6}$-alkoxy, $C_{1-6}$-alkenyl, trifluoromethyl, $C_{3-5}$-alkylene, aryloxy or aralkoxy; and $R^1$ and $R^2$ are $C_{1-10}$-alkyl, $C_{3-7}$-cycloalkyl, $C_{2-10}$-alkenyl, $C_{3-6}$-cycloalkyl $C_{1-5}$-alkyl, unsubstituted or substituted with $C_{1-5}$-alkoxy, or cyano; or $R^1$ and $R^2$ may together form a carbocyclic ring and a salt thereof with a pharmaceutically acceptable acid, provided however that $R^1$ is not $C_{3-7}$-cycloalkyl, $C_{3-10}$-alkyl, or alkenyl which may be straight, branched or cyclic, unsubstituted or substituted with $C_{1-4}$-alkoxy, aryloxy or cycloalkyl or cycloalkylalkyl, when X is H and $R^2$ is a methyl group.

Alkyl is intended to mean straight or branched alkyl radicals.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts.

The invention also relates to a method of preparing the above mentioned compounds. This methods comprises a) reacting a compound having the general formula II

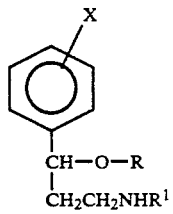

wherein $R^1$ and R have the meaning defined above, with a compound having the general formula $R^2$-Y, wherein Y is a leaving group such as halogen and $R^2$ has the meaning defined above, and b) reacting a compound having the formula III

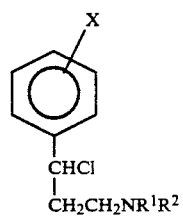

with a compound having the formula IV

ROH           (IV)

wherein R, $R^1$ and $R^2$ have the meaning defined above, giving compounds of the general formula V

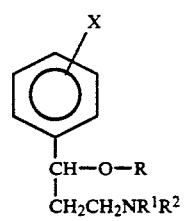

and c) preparing compounds having the formula III from the corresponding hydroxy compound by means of $SOCl_2$. The hydroxy compounds being prepared by a $NaBH_4$ reduction of the corresponding oxo-compound, which is prepared by a Mannich reaction d) preparing compounds of the general formula II by demethylating compounds of the general formula V by means of $ClCOOCHClCH_3$ e) reacting a compound having the general formula

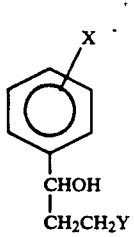

VI with a compound having the general formula R¹NHR² wherein X, R¹ and R² have the meaning defined above, and Y is a leaving group such as halogen f) Reacting a compound having the general formula

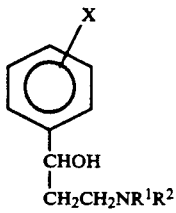

with a compound having the general formula

wherein X, R¹ and R² have the meaning defined above.

The pharmacological properties of the compounds of the invention can be illustrated by determining their capability to inhibit calcium uptake into brain synaptosomes.

PRINCIPLE

Depolarization of neuronal membranes leads to an opening of socalled 'voltage operated calcium channels' (VOC) in the membranes which allows a massive influx of calcium from the extracellular space. A crude synaptosomal preparation (socalled $P_2$ fraction) contains small vesicles surrounded by neuronal membrane and it is possible in such a preparation to study a depolarization-induced opening of VOC. In the present model $^{45}Ca$ influx is induced in the synaptosomes by depolarization with elevated potassium concentrations, and the effect of test substances on this stimulated uptake is studied (Nachshen, D.A. and Blaustein, M.P., Mol. Pharmcol., 16, 579 (1979)).

ASSAY

A male Wistar rat is decapitated and the cerebral cortex removed and homogenized in 20 ml. of ice-cold 0.32 M sucrose using a glass homogenizer with a teflon pestle. All subsequent steps for isolation of synaptosomes are done at 0°-4° C. The homogenate is centrifuged at 1000 x g for 10 min and the resulting supernatant is re-centrifuged at 18000 x g for 20 min. This pellet ($P_2$) is resuspended in 0.32 M sucrose (10 ml per g of original tissue) with a teflon pestle.

Aliquots (0.050 ml) of this crude synaptosomal suspension are added to glass tubes containing 0.625 ml of NaCl buffer (136 mM NaCl, 4 mM KCl, 0.35 mM $CaCl_2$, 1.2 mM $MgCl_2$, 20 mM Tris HCl, 12 mM glucose, pH 7.4) and 0.025 ml of various drug solutions in 48% Ethanol. The tubes are pre-incubated for 30 min on ice and then for 6 min at 37° C. in a water bath. The uptake is immediately initiated by adding 0.4 ml of $^{45}CaCl_2$ (specific activity=29-39 Ci/g; 0.5 Ci/assay), in 145 mM NaCl for non-depolarized samples and in 145 mM KCl for depolarized samples. The incubation is continued for 15 s.

The uptake is terminated by rapid filtration through GF-C glass fiber filters which are washed three times with 5 ml of a cold solution containing 145 mM KCl, 7 mM EGTA and 20 mM Tris HCl, pH 7.4. The amount of radioactivity on the filter disc is determined by liquid scintillation spectrometry.

TEST PROCEDURE

Test substances are dissolved in 10 ml of 48% ethanol at a concentration of 0.44 mg/ml. Dilution are made in 48% ethanol to give final concentrations of 0.1, 0.3, 1, 3 and 10 μg/ml. Experiments are performed in duplicate. Controls for depolarized and nondepolarized samples are included in the assay and test substances are only tested in depolarized samples.

RESULTS

The test value will be given as MEC (the minimum concentration (μg/ml) of test substance which inhibit stimulated uptake of $^{45}Ca$ significantly different from control ($P<0.05$, Student's t-test).

Test results obtained by testing some compounds of the present invention will appear from the following table 1.

TABLE 1

| Compound | MEC (μg/ml) |
| --- | --- |
| 11 | 1 |
| 12 | 1 |
| 8 | >1 |
| 13 | 1 |
| 18 | 1 |
| 21 | >1 |
| 22 | ≧1 |
| 25 | 0.3 |

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration: or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective calcium overload blocking amount of the active ingredient commensurate with the intended daily dosage range to be employed. Tablets containing ten (10) milligrams of active ingredient or, more broadly, ten (10) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty, acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir of the like can be used in cases where a sweetened vehicle can be employed.

Generally, the compounds of this invention are dispensed in unit form comprising 0.05-100 mg in a pharmaceutically acceptable carrier per unit dosage.

The dosage of the compounds according to this invention is 0.1-300 mg/day, preferably 10-100 mg/day, when administered to patients, e.g. humans, as a drug.

A typical tablet which may be prepared by conventional tabletting techniques contains:

| Active compound | 5.0 mg |  |
|---|---|---|
| Lactosum | 67.8 mg | Ph.Eur. |
| Avicel ® | 31.4 mg |  |
| Amberlite ® IRP 88 | 1.0 mg |  |
| Magnesii stearas | 0.25 mg | Ph.Eur. |

Due to the high calcium overload blocking activity, the compounds of the invention are extremely useful in the treatment of symptoms related to an accumulation of calcium in brain cells of mammals, when administered in an amount effective for blocking calcium overload in brain cells. The important calcium overload blocking activity of compounds of the invention includes both activity against anoxia, ischemia migraine epilepsy traumatic injury and neurodegenerative diseases. The compounds of the invention may accordingly be administered to a subject, e.g., a living animal body, including a human, in need of a calcium overload blocker, and if desired in the form of a pharmaceutically acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective calcium overload blocking amount, and in any event an amount which is effective for the treatment of anoxia, ischemia, migraine, epilepsy, traumatic injury or neurodegenerative diseases due to their calcium overload blocking activity. Suitable dosage ranges are 0.1-300 milligrams daily, preferably 10-100 milligrams daily, and especially 30-70 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1

(+−)

N-2-cyanoethyl-N-methyl-3-(3,4-methylenedioxyphenoxy)-3-phenylpropylamine, oxalate (compound 1)

The title compound was prepared from (+−) N-methyl-3-(3,4-methylenedioxyphenoxy)-3-phenylpropylamine (0.5 g) potassium carbonate (2 g) and 3-bromopropionitrile (2 ml) by reflux in abs. ethanol (50 ml) for 3 h. The mixture was cooled and filtered. The filtrate was evaporated to dryness and subsequently dilute NaOH was added and extracted with ether. The etheral layer was dried (MgSO$_4$) and evaporated to dryness. The title compound was precipitated as the oxalate by mixing with an equimolar amount of anhydrous oxalic acid in acetone solution. M.p. 125°-127° C.

(+−)

N-4-cyanobutyl-N-methyl-3-(3,4-methylene-dioxyphenoxy)-3-phenylpropylamine, oxalate (compound 2)

Was prepared as described above using 5-bromovaleronitrile as the alkylating agent. Reflux for 14 h. Purification on a silicagel using CH$_2$Cl$_2$/CH$_3$OH 9/1 as eluent. M.p. 114°-116° C.

EXAMPLE 2

(+−)

N,N-dimethyl-3-(3-trifluoromethylphenoxy)-3-(4-fluorophenyl) propylamine, oxalate (compound 3)

4-fluoroacetophenone (48.3 g), dimethylamine hydrochloride (37 g), paraformaldehyde (13.6 g) and conc. HCl (0.75 ml) was refluxed in 96% ethanol (57 ml) for 4 h. The mixture was subsequently stirred at R.T. overnight resulting in a precipitate. This was isolated and washed with ether and acetone resulting in 68.2 g of 3-dimethylamino-1-(4-fluorophenyl)propanal hydrochloride (compound 4).

35 g of (compound 4) was converted to the amine by means of OH$^−$/ether extraction and reduced with NaBH$_4$ (2.2 g) in abs. ethanol (200 ml) by stirring at R.T. for 20 h. The mixture was evaporated to dryness and the residue extracted with OH$^−$/CH$_2$Cl$_2$. Evaporation of the CH$_2$Cl$_2$ phase gave 23.2 g of (+−) 3-dimethylamino-1-(4-fluorophenyl)-1-propanol (compound 5). Identified by $^1$H NMR.

(Compound 5) was dissolved in CH$_2$Cl$_2$ (200 ml). The solution was saturated with HCl (g) and thionyl chloride (20 ml in 50 ml CH$_2$Cl$_2$) was added dropwise. Stirring at R.T. overnight and subsequent evaporation gave a crystalline compound which was washed with acetone. The resulting crystals were identified as (+−) 3-chloro-N,N-dimethyl-3-(4-fluorophenyl)propyl amine, hydrochloride (compound 6) by $^1$H NMR.

5.3 g of (compound 6) was added to a solution of 3-trifluoromethylphenol (6.8 g) and NaOH (2 g) in abs. ethanol (100 ml). Reflux for 10 h. The mixture was subsequently filtered and evaporated, extracted with $OH^-/CH_2Cl_2$ and the $CH_2Cl_2$ phase was dried and evaporated. The resulting oil was precipitated as the oxalate from acetone solution. M.p. 155°–156° C. identified as (+−) N,N-dimethyl-3-(3-trifluoromethylphenoxy)-3-(4-fluorophenyl) propylamine, oxalate (compound 3) by $^1H$ NMR.

(+−)
N-methyl-3-(3-trifluoromethylphenoxy)-3-(4-fluorophenyl) propylamine, hydrochloride (compound 8)

3 g of (compound 3) as the base was dissolved in dry toluene (50 ml). 1-Chloroethyl chloroformate (1.4 ml) was added dropwise and the mixture stirred for 3 h at 50° C. and subsequently at 80° C. for 1 h. The mixture was evaporated, $CH_3OH$ (50 ml) wa added and the solution refluxed for 8 h. The solution was evaporated to dryness and the residue was crystallized from petrol ether. M.p. 97°–102° C.

(+−)
N-cyclopropylmethyl-N-methyl-3-(3-trifluoromethylphenoxy)-3-(4-fluorophenyl) propylamine, oxalate (compound 9)

This compound was prepared from (compound 8) and cyclopropylmethylbromide as described in example 1. Reflux time 5 h. M.p. 134°–136° C.

(+−)
N-butyl-N-methyl-3-(3-trifluoromethylphenoxy)-3-(4-fluorophenyl) propylamine, oxalate (compound 10)

Preparation from (compound 8) and 1-bromobutane as described in example 1. Reflux time 6 h. M.p. 138°–142° C.

EXAMPLE 3

(+−)
N,N-dimethyl-3-(5,6,7,8-tetrahydro-2-naphthoxy)-3-(4fluorophenyl) propylamine, oxalate (compound 7)

Was prepared from (compound 6) and 5,6,7,8-tetrahydro-2naphthol as described for (compound 3). Reflux for 10 h. M.p. 179°–183° C.

(+−)
N-cyclopropylmethyl-N-methyl-3-(4-fluorophenyl)-3-(5,6,7,8-tetrahydro-2-naphthoxy) propylamine, oxalate (compound 11)

N-methyl-3-(4-fluorophenyl)-3-(5,6,7,8-tetrahydro-2-naphthoxy) propylamine, oxalate (1.2 mmol), cyclopropylmethylbromide (1.2 ml) and $K_2CO_3$ (1 g) were refluxed in abs. ethanol (25 ml) for 4 h. Rinse up as described in example 1 gave (compound 11). M.p. 112° C.

(+−)
N-butyl-N-methyl-3-(4-fluorophenyl)-3-(5,6,7,8-tetrahydro-2-naphthoxy) propylamine, oxalate (compound 12)

Preparation as described for (compound 11). Reflux time 7 h. M.p. 142°–146° C.

EXAMPLE 4

(+−)
N-butyl-3-(4-trifluoromethylphenoxy)-3-phenylpropylamine, oxalate (compound 13)

3-Chloropropiophenone (25.2 g) was dissolved in abs. ethanol (200 ml), $NaBH_4$ (2.2 g) was slowly added and the mixture stirred overnight at R.T. The mixture was filtered and the filtrate evaporated to dryness. $H_2O$ was added and the solution extracted with ether, the ether phase dried ($MgSO_4$) and evaporated. The resulting oil purified on silioagel $CH_2Cl_2$ as eluent giving 3-chloro-1-phenyl-1-propanol (compound 14), identified by $^1H$ NMR.

(Compound 14) (10.1 g) was dissolved in acetone (200 ml) saturated with NaI. The mixture was refluxed for 12 h and subsequently stirred at RT for 3 days. The mixture was evaporated to dryness and the residue extracted with $H_2O$/ether. The etheral layer separated and washed with $H_2O$ and saturated NaCl-solution. Resulting in 12.5 g of 3-iodo-1-phenyl-1-propanol (compound 15).

(Compound 15) (12.5 g) was treated with butylamine (40 ml) in THF (75 ml) at RT for 4 h. The mixture evaporated and the residue extracted with $OH^-$/ether. The ether phase washed with $H_2O$ and saturated NaCl-solution, dried ($MgSO_4$) and evaporated giving 6.2 g of 3-butylamino-1-phenyl-1-propanol (compound 16). Identified by $^1H$ NMR.

(Compound 16) (4.7 g) was dissolved in dimethyl acetamide (50 ml), NaH (ether washed, 1 g) was added and the solution heated to 70° C. for 0.5 h. 4-fluorobenzotrifluoride (4.0 g) was added and the mixture heated at 90° C. for 6 h. Subsequently $H_2O$ (150 ml) was added and the mixture extracted with $CH_2Cl_2$. The organic phase was washed with $H_2O$ and saturated NaCl-solution, dried and evaporated. The resulting oil (8.5 g) was purified on silicagel using $CH_2Cl_2/CH_3OH$ 9/1 as eluent. Precipitation with oxalic acid (anh.) in acetone solution gave (compound 13). M.p. 183°–4° C.

(+−)
N-butyl-N-ethyl-3-(4-trifluoromethylphenoxy)-3-phenylpropylamine, oxalate (compound 17)

Preparation from (compound 13) and ethyliodide by reflux for 3 h as described in example 1. M.p. 139°–141° C.

(+−)
N,N-dibutyl-3-(4-trifluoromethylphenoxy)-3-phenylpropylamine, oxalate (compound 18)

Preparation from (compound 13) and 1-bromobutane as described in example 1. Reflux for 10 h. M.p. 128.6° C.

(+−)
N-butyl-N-cyclopropylmethyl-3-(4-trifluoromethylphenoxy)-3-phenylpropylamine, oxalate (compound 19)

Prepared by reaction of (compound 13) and cyclopropylmethylbromide as described in example 1. Reflux for 10 h. M.p. 124°–126° C.

EXAMPLE 5

(+ −)
N-butyl-3-(2-trifluoromethylphenoxy)-3-phenyl-propylamine, oxalate (compound 20)

Prepared from (compound 16) and 2-fluorobenzotrifluoride as described for (compound 13). Heating to 70° C. for 24 h. M.p. 160°–165° C.

(+ −)
N-butyl-N-cycloprop-vlmethyl-3-(2-trifluoromethyl-phenoxy)-3-phenylpropylamine, oxalate (compound 21)

Preparation from (compound 20) and cyclopropylmethylbromide as described in example 1. Reflux for 4 h. M.p. 90°–96° C.

EXAMPLE 6

(+ −)
3-(4-cyanophenyl)-N,N-dimethyl-3-(4-trifluoromethyl-phenoxy) propylamine, oxalate (compound 22)

Was prepared from 4-cyanoacetophenone using the reaction described for (compound 4) giving 1-(4-cyanophenyl)-3-dimethylaminopropanal (compound 23) and further reaction to 1-(4-cyanophenyl)-3-dimethylaminopropanol (compound 24) as described for (compound 5) and finally reaction to (compound 22) with 4-fluorobenzotrifluoride as described for (compound 13). M.p. 138°–140° C.

EXAMPLE 7

(+ −)
3-(4-cyanophenyl)-N,N-dimethyl-3-(5,6,7,8-tetrahydro-2-naphthoxy) propylamine, hydrochloride (compound 25)

3-chloro-3-(4-cyanophenyl)-N,N-dimethylpropylamine (compound 26) was prepared from (compound 24) by means of $SOCl_2$ as described for (compound 6).

(Compound 25) was subsequently prepared by treating (compound 26) with 5,6,7,8-tetrahydro-2-naphthol as described for the preparation of (compound 3). Reflux time 2 days. M.p. 132° C.

EXAMPLE 8

(+ −)
N,N-dimethyl-3-(4-methoxyphenyl)-3-(4-trifluoromethylphenoxy)propylamine, oxalate (compound 29)

This was prepared from 4-methoxyacetophenone using the reaction described for (compound 4) giving 1-(4-methoxyphenyl)-3-dimethylaminopropanal (compound 27), further reaction to 1-(4-methoxyphenyl)-3-dimethylaminopropanol (compound 5) and finally reaction to (compound 29) with 4-fluorobenzotrifluoride by means of NaH as described for (compound 13). M.p. 146°–148° C.

What is claimed is:

1. A method of treating calcium overload in brain cells of mammals comprising administering an effective amount of a compound of formula I

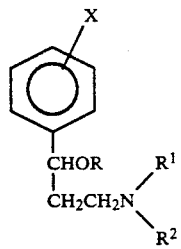

(I)

wherein
X is H, cyano, halogen, $C_{1-6}$-alkoxy, $C_{1-6}$alkyl or $C_{3-5}$-alkylidene;
R is 3,4-methylenedioxyphenyl and phenyl which are optionally substituted with cyano, halogen, $C_{1-6}$-alkyl, $C_{1-6}$-alkoxy, $C_{2-6}$-alkenyl, trifluoromethyl or $C_{3-5}$-alkylidene; and
$R^1$ and $R^2$ independently are $C_{1-10}$-alkyl, $C_{3-7}$-cycloalkyl, $C_{2-10}$-alkenyl or $C_{3-6}$-cycloalkyl-$C_{1-5}$-alkyl which are optionally substituted with $C_{1-5}$-alkoxy or cyano;
provided that $R^1$ is not $C_{3-7}$-cycloalkyl, $C_{1-10}$-alkyl or $C_{2-10}$-alkenyl which are optionally substituted with $C_{1-4}$-alkoxy, when X is H and $R^2$ is a methyl group; or a pharmaceutically acceptable salt thereof.

2. The method according to claim 1, wherein the compound of formula I is 3-(4-cyanophenyl)-N,N-dimethyl-3-(5,6,7,8-tetrahydro-2-naphthoxy) propylamine or a pharmaceutically acceptable salt thereof.

3. The method according to claim 1, wherein the compound of formula I is N-butyl-N-methyl-3-(4-fluorophenyl)-3-(5,6,7,8-tetrahydro-2-naphthoxy) propylamine or a pharmaceutically acceptable salt thereof.

4. The method according to claim 1, wherein the compound of formula I is N,N-dibutyl-3-(4-trifluoromethylphenoxy)-3-phenylpropylamine or a pharmaceutically acceptable salt thereof.

5. The method according to claim 1, wherein the compound of formula I is N-cyclopropylmethyl-N-methyl-3-(4-fluorophenyl)-3-(5,6,7,8-tetrahydro-2-naphthoxy) propylamine or a pharmaceutically acceptable salt thereof.

* * * * *

UNITED STATES PATENT AND TRADEMARK OFFICE
CERTIFICATE OF CORRECTION

PATENT NO.     : 5,145,870
DATED          : September 8, 1992
INVENTOR(S)    : Jakobsen et al.

It is certified that error appears in the above-identified patent and that said Letters Patent is hereby corrected as shown below:

On the title page: item

Abstract, line 12 of text: after "cyano;" insert between paragraphs --or--

Col. 7, line 21: delete "wa" and insert --was--

Col. 9, line 11: delete "cycloprop-vlmethyl" and insert --cyclopropylmethyl--

Signed and Sealed this

Thirtieth Day of November, 1999

Attest:

Q. TODD DICKINSON

Attesting Officer

Acting Commissioner of Patents and Trademarks